US008044221B2

(12) United States Patent
Saito

(10) Patent No.: US 8,044,221 B2
(45) Date of Patent: Oct. 25, 2011

(54) FLUORINE-CONTAINING BORONIC ACID ESTER COMPOUND AND METHOD FOR PRODUCING THE SAME

(75) Inventor: Satoru Saito, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 13/063,012

(22) PCT Filed: Aug. 31, 2009

(86) PCT No.: PCT/JP2009/065152
§ 371 (c)(1),
(2), (4) Date: Mar. 9, 2011

(87) PCT Pub. No.: WO2010/029868
PCT Pub. Date: Mar. 18, 2010

(65) Prior Publication Data
US 2011/0166375 A1 Jul. 7, 2011

(30) Foreign Application Priority Data
Sep. 9, 2008 (JP) ................................. 2008-230515

(51) Int. Cl.
C07D 321/00 (2006.01)
(52) U.S. Cl. .................................................... 549/213
(58) Field of Classification Search .................. 549/213
See application file for complete search history.

(56) References Cited

FOREIGN PATENT DOCUMENTS
JP 07-126323 5/1995

OTHER PUBLICATIONS

Miyaura, Norio, et al., Palladium-Catalyzed Cross-Coupling Reactions of Organoboron Compounds, Chem. Rev., vol. 95, (1995), pp. 2457-2483.
Morgan, Alexander, et al., Synthesis, Flame-Retardancy Testing, and Preliminary Mechanism Studies of Nonhalogenated Aromatic Boronic Acids: A New Class of Condensed-Phase Polymer Flame-Retardant Additives for Acrylonitrile-Butadiene-Styrene and Polycarbonate, J. Appl. Poly. Sci., vol. 76, (2000), pp. 1257-1268.
Registry (Stn) [online], Jun. 7, 2001 [retrieval date Sep. 9, 2009] CAS registry No. 340036-45-5, 1 pg.
Registry (Stn) [online], Jun. 8, 2001 [retrieval date Sep. 9, 2009] CAS registry No. 340132-47-0, 1 pg.
International Search Report from corresponding PCT application No. PCT/JP2009/065152 dated Sep. 29, 2009, 2 pgs.
International Preliminary Report on Patentability and Written Opinion from corresponding PCT application No. PCT/JP2009/065152 dated Apr. 28, 2011, 5 pgs.

Primary Examiner — Rebecca Anderson
Assistant Examiner — Samantha Shterengarts
(74) Attorney, Agent, or Firm — Brinks Hofer Gilson & Lione

(57) ABSTRACT

A fluorine-containing boronic acid ester represented by the general formula:

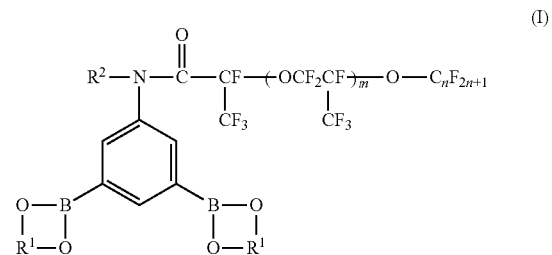

($R^1$ is a linear or branched divalent aliphatic hydrocarbon group having 2 to 10 carbon atoms, $R^2$ is a hydrogen atom, an alkyl group having 1 to 3 carbon atoms or phenyl group, n is an integer of 1 to 3, and m is an integer of 0 to 4) having an improved solubility in organic solvents is produced by reacting a fluorine-containing 3,5-dihalogenoanilide derivative represented by the general formula:

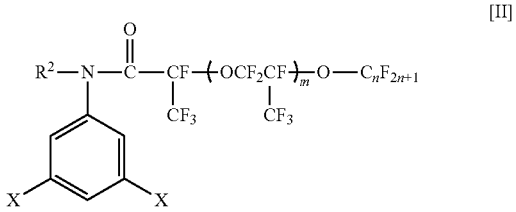

($R^2$ is a hydrogen atom, an alkyl group having 1 to 3 carbon atoms or phenyl group, X is a halogen atom, n is an integer of 1 to 3, and m is an integer of 0 to 4) with a dialkoxyborane represented by the general formula:

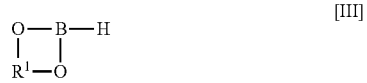

($R^1$ is a linear or branched divalent aliphatic hydrocarbon group having 2 to 10 carbon atoms).

8 Claims, No Drawings

FLUORINE-CONTAINING BORONIC ACID ESTER COMPOUND AND METHOD FOR PRODUCING THE SAME

RELATED APPLICATION

This application is a 35 U.S.C. §371 national phase filing of International Patent Application No. PCT/JP2009/065152, filed Aug. 31, 2009, through which and to which priority is claimed under 35 U.S.C. §119 to Japanese Patent Application No. 2008-230515, filed Sep. 9, 2008.

TECHNICAL FIELD

The present invention relates to a fluorine-containing boronic acid ester compound and a method for producing the same. More particularly, the present invention relates to an aromatic fluorine-containing boronic acid ester compound that can suitably be used as a starting material for the production of conjugated polymer materials or as a curing agent of elastomeric polymer materials, and a method for producing the same.

BACKGROUND ART

Organic boronic acids or ester compounds thereof are stable in water and air, and are utilized in cross-coupling reactions using a transition metal complex as a catalyst. Particularly, the reaction using a palladium compound as a catalyst is known as the Suzuki-Miyaura reaction, which is industrially used in pharmaceutical synthesis, pesticide synthesis, liquid crystal material synthesis, and the like. (see Non-Patent Document 1).

Moreover, recently, aromatic diboronic acids or ester compounds thereof are often used in the investigation study of OLED and conductive polymer materials. However, it is difficult to purify aromatic diboronic acids because many of them contain boroxine as an impurity. There is another drawback that aromatic diboronic acids or ester compounds are converted into boroxine by heating, thereby reducing the reactivity. In contrast, it is easy to purify aromatic diboronic acid ester compounds; however, many of them are poorly soluble in organic solvents and have a very high melting point.

PRIOR ART DOCUMENT

Non-Patent Document

Non-Patent Document 1: Chem. Rev., vol. 95, pp. 2457 (1995)

Non-Patent Document 2: J. Appl. Poly. Sci., vol. 76, pp. 1257 (2000)

OUTLINE OF THE INVENTION

Problem to be Solved by the Invention

An object of the present invention is to provide an aromatic fluorine-containing diboronic acid ester compound that has an improved solubility in organic solvents and that is in the form of a low-melting-point solid or liquid, and a method for producing the same.

Means for Solving the Problem

The present invention provides a fluorine-containing boronic acid ester compound represented by the general formula:

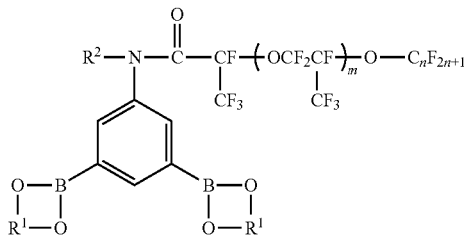

wherein $R^1$ is a linear or branched divalent aliphatic hydrocarbon group having 2 to 10 carbon atoms, $R^2$ is a hydrogen atom, an alkyl group having 1 to 3 carbon atoms or phenyl group, n is an integer of 1 to 3, and m is an integer of 0 to 4.

The fluorine-containing boronic acid ester compound is produced by the reaction of a fluorine-containing 3,5-dihalogenoanilide derivative represented by the general formula:

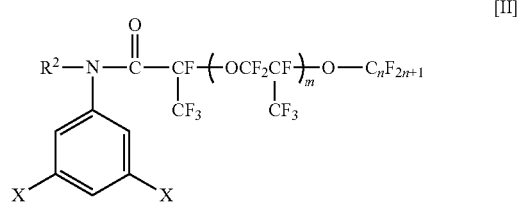

with a dialkoxyborane represented by the general formula:

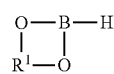

wherein $R^1$ is a linear or branched divalent aliphatic hydrocarbon group having 2 to 10 carbon atoms.

Effect of the Invention

The fluorine-containing boronic acid ester compound of the present invention is highly soluble in organic solvents, and is in the form of a low-melting-point solid or liquid having a melting point of about 0 to 150° C. The fluorine-containing boronic acid ester compound can suitably be used as a starting material for the production of conjugated polymer materials or as a curing agent of elastomeric polymer materials.

EMBODIMENTS FOR CARRYING OUT THE INVENTION

The fluorine-containing boronic acid ester compound of the present invention is represented by the general formula:

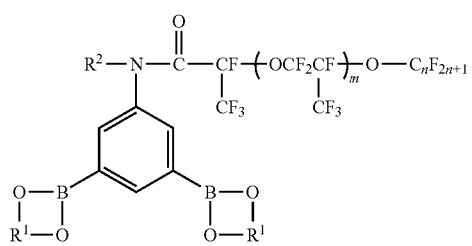

[I]

In the fluorine-containing boronic acid ester compound [I], $R^1$ is a linear or branched divalent aliphatic hydrocarbon group having 2 to 10 carbon atoms. Examples of $R^1$ include —$CH_2C(CH_3)_2CH_2$—, —$CH_2CH_2CH_2$—, —$C(CH_3)_2CH_2C(CH_3)_2$—, —$C(CH_3)_2CH_2CH(CH_3)$—, —$C(CH_3)_2C(CH_3)_2$—, and the like groups; particularly, —$C(CH_3)_2C(CH_3)_2$— group is selected in terms of ease of production. $R^2$ is a hydrogen atom, an alkyl group having 1 to 3 carbon atoms or phenyl group; among these, a methyl group is particularly preferred. n is an integer of 1 to 3, and m is an integer of 0 to 4.

Specific examples of the fluorine-containing boronic acid ester compound [I] wherein n is 3 include those shown below.

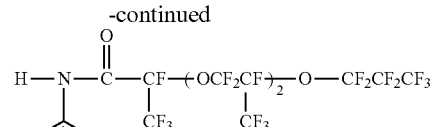

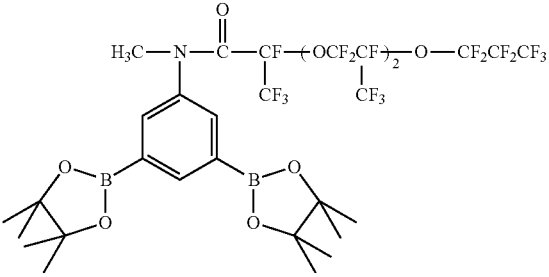

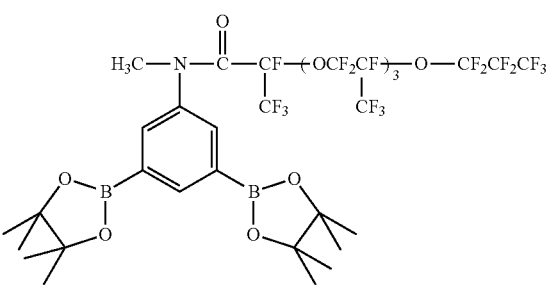

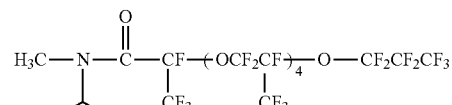

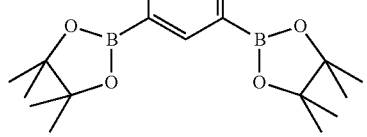

Additionally, examples of the fluorine-containing boronic acid ester compound [I], wherein n is 1 or 2, include those shown below.

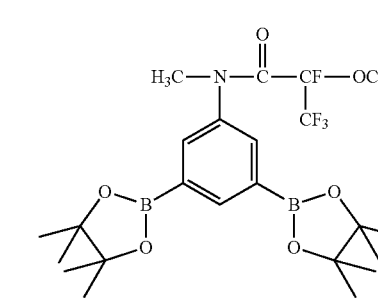

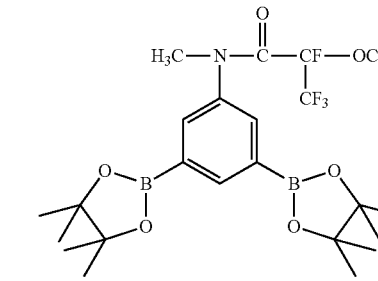

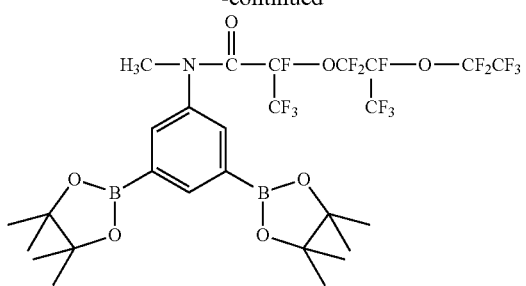

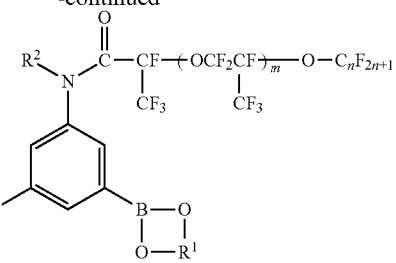

Note: Ni(dppp)Cl$_2$: [1,3-bis(diphenylphosphino)propane]dichloronickel

The borylation reaction of the second step is carried out by reacting a fluorine-containing 3,5-dihalogenoanilide derivative with a dialkoxyborane using a Group-10 transition metal catalyst.

In the fluorine-containing 3,5-dihalogenoanilide derivative [II], X is a halogen atom selected from the group of iodine, bromine, chlorine, and fluorine. Among these, bromine or iodine is preferred, and particularly bromine is most preferred.

Examples of usable dialkoxyboranes [III] include 4,4,5,5-tetramethyl-1,3,2-dioxaborolane, 4,4,6-trimethyl-1,3,2-dioxaborinane, 4,4,6,6-tetramethyl-1,3,2-dioxaborinane, 5,5-dimethyl-1,3,2-dioxaborinane, 1,3,2-dioxaborinane, and the like. In consideration of the chemical stability and ease of handling of the produced boronic acid ester compound, 4,4,5,5-tetramethyl-1,3,2-dioxaborolane is preferred.

As the Group-10 transition metal catalyst used in the reaction, a nickel or palladium catalyst can be used. Examples of nickel catalysts include
[1,2-bis(diphenylphosphino)ethane]dichloronickel,
[1,3-bis(diphenylphosphino)propane]dichloronickel,
[1,4-bis(diphenylphosphino)butane]dichloronickel,
[1,1'-bis(diphenylphosphino)ferrocene]dichloronickel,
bis(triphenylphosphine)dichloronickel, and the like.

Examples of palladium catalysts include
bis(dibenzylideneacetone)palladium,
[1,1'-bis(diphenylphosphino)ferrocene]dichloropalladium,
tetrakis(triphenylphosphine)palladium,
palladium acetate, and the like.

A suitable catalyst is a nickel catalyst, and particularly [1,3-bis(diphenylphosphino)propane]dichloronickel is preferable. The nickel catalyst is used at a ratio of about 0.1 to 20 mol %, and preferably about 1 to 10 mol %, based on the fluorine-containing 3,5-dihalogenoanilide derivative.

In the borylation reaction, hydrogen halide is produced as a by-product, and it is therefore necessary to add a base in an amount of stoichiometry or higher as a scavenger. Examples of bases include alkali metal salts of organic acids such as potassium acetate, alkali metal salts of phenols such as potassium phenolate, inorganic acid alkali metal salts such as potassium phosphate and potassium carbonate, and tertiary amines such as triethylamine and diisopropylethylamine; among these, tertiary amines are preferred because the side reaction is suppressed, and triethylamine is particularly preferred.

The reaction is carried out in a toluene solvent under an inert gas (e.g., nitrogen) atmosphere at about 80 to 110° C. for about 6 to 48 hours (see Non-Patent Document 2).

The resulting fluorine-containing boronic acid ester compound can be reacted with, for example, dihalogenated benzene to synthesize polyphenylene, which is a conjugated polymer material.

These examples of the fluorine-containing boronic acid ester compound [I] can be produced, for example, by the following process.

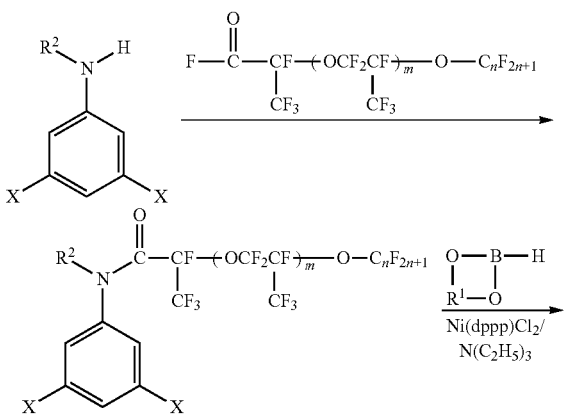

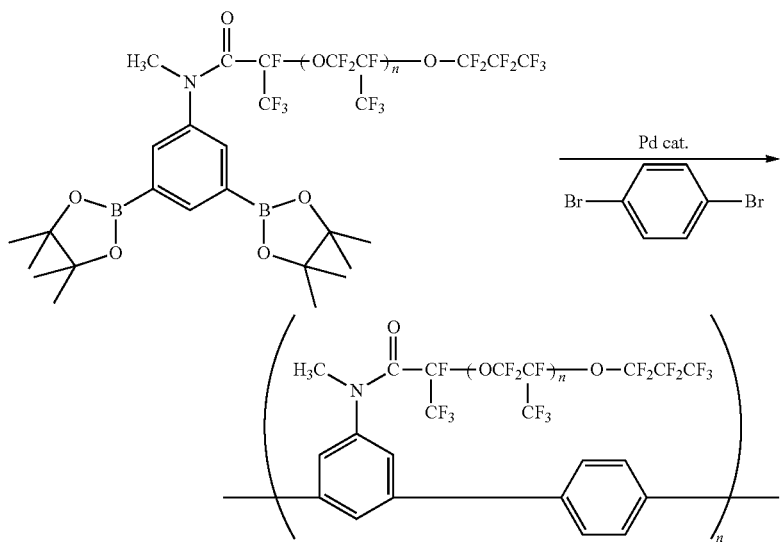

Moreover, the fluorine-containing boronic acid ester compound can be reacted with, for example, the following fluorine-containing polyether compound to produce an elastomeric cured product.

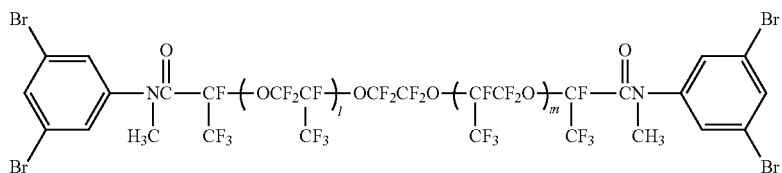

The elastomeric cured products obtained therefrom are excellent in chemical resistance, heat resistance, and low-temperature characteristics, and can be used in the automobile industry, semiconductor production industry, aircraft industry, and the like.

EXAMPLES

The following describes the present invention with reference to examples.

Reference Example 1

Synthesis of Reaction Starting Material

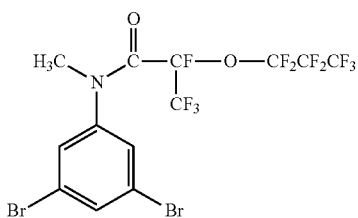

To 30 ml of a 1,2-dimethoxyethane solution in which 4.5 g (17 mmol) of 3,5-dibromo-N-methylaniline and 2.4 g (24 mmol) of triethylamine were dissolved, 6.9 g (21 mmol) of 2-perfluoropropoxy perfluoropropionic acid fluoride of the formula: $CF_3CF_2CF_2OCF(CF_3)COF$ was added dropwise, and the mixture was reacted at room temperature for 2 hours.

After a general reaction treatment was carried out, the crude product was distilled under reduced pressure, thereby obtaining 8.0 g (yield based on 3,5-dibromo-N-methylaniline: 80%) of 3,5-dibromo-N-methylanilide compound as a light yellow liquid.

Example 1

Synthesis of Fluorine-Containing Boronic Acid Ester Compound

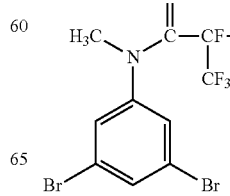 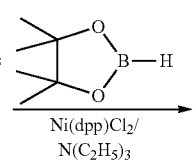

-continued

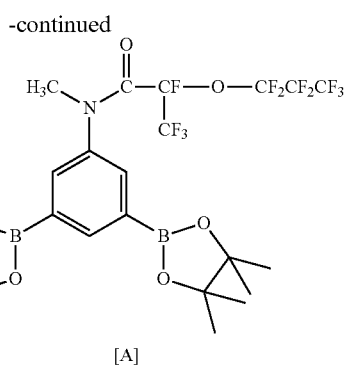

[A]

To a toluene (120 ml) solution in which 8.0 g (14 mmol) of 3,5-dibromo-N-methylanilide compound obtained in Reference Example 1, 0.38 g (0.70 mmol) of [1,3-bis(diphenylphosphino)propane]dichloronickel, and 8.4 g (83 mmol) of triethylamine were dissolved, 5.9 g (46 mmol) of 4,4,5,5-tetramethyl-1,3,2-dioxaborolane was added dropwise at a temperature of 80° C. Subsequently, the temperature was raised to 100° C., and the mixture was reacted in a nitrogen atmosphere for 44 hours. The reaction mixture was cooled to room temperature, and then added to an aqueous saturated ammonium chloride solution to terminate the reaction. Then, a general reaction treatment was carried out, and 10.3 g of a crude product was obtained.

The product was isolated by column chromatography (Wakogel C-300) using a mixed solvent of n-hexane/diethyl ether (volume ratio: 1/1) as an elute, and then recrystallized with ethanol. Thus, 7.2 g (yield based on 3,5-dibromo-N-methylanilide compound: 77%) of a target fluorine-containing boronic acid ester compound [A] was obtained as a white crystal.

Melting point: 124 to 128° C.

IR (KBr): 2,981 $cm^{-1}$, 1,698 $cm^{-1}$, 1,602 $cm^{-1}$, 1,450 $cm^{-1}$, 1,243 $cm^{-1}$, 1,142 $cm^{-1}$

The following shows the chemical shifts of $^{19}$F-NMR (chemical shift: $CFCl_3$ basis) and $^1$H-NMR (chemical shift: TMS basis), measured in $CDCl_3$:

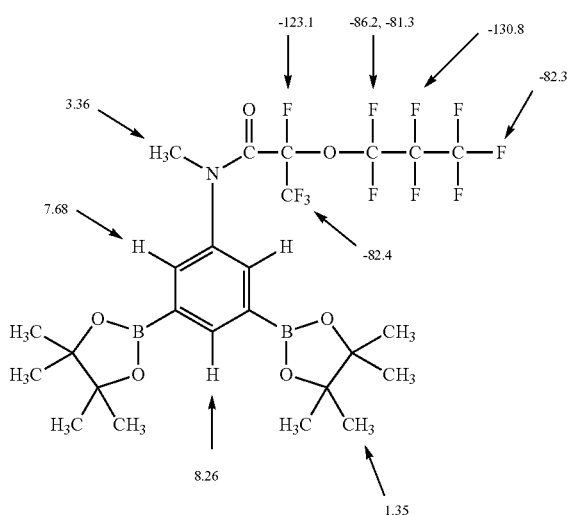

The solubility of the fluorine-containing boronic acid ester compound [A] in 1,3-bis(trifluoromethyl)benzene, which was a fluorine-containing organic solvent used in Reference Example 3, described later, was 3.0 g/10 ml·solvent. Here, the solubility was determined in such a manner that the compound was added and stirred in 10 ml of said fluorine-containing organic solvent at 25° C., and then the maximum amount of addition sufficient to make the solution homogeneous was visually measured.

In contrast, the solubility of 1,4-bis(4,4,5,5-tetramethyl-1,3,2-dioxaborolan-2-yl)benzene (melting point: 240° C.), which was an aromatic diboronic acid ester compound, in said fluorine-containing organic solvent was 0.17 g/10 ml·solvent, and 1,4-benzene diboronic acid (melting point: 300° C. or more), which was an aromatic diboronic acid, was insoluble in said fluorine-containing organic solvent.

Reference Example 2

Synthesis of Reaction Starting Material

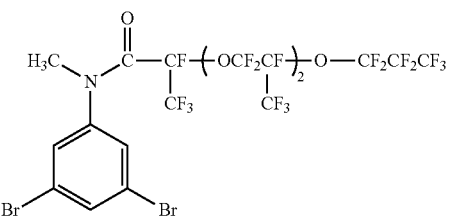

To 40 ml of a 1,2-dimethoxyethane solution in which 6.0 g (23 mmol) of 3,5-dibromo-N-methylaniline and 3.3 g (33 mmol) of triethylamine were dissolved, 18 g (27 mmol) of 2-$C_3F_7O[CF(CF_3)CF_2O]_2$-substituted perfluoropropionic acid fluoride of the formula: $CF_3CF_2CF_2O[CF(CF_3)CF_2O]_2$ $CF(CF_3)COF$ was added dropwise, and the mixture was reacted at room temperature for 1 hour. After a general reaction treatment was carried out, the crude product was distilled under reduced pressure, thereby obtaining 17.5 g (yield based on 3,5-dibromo-N-methylaniline: 85%) of 3,5-dibromo-N-methylanilide compound as a transparent and colorless liquid.

Example 2

Synthesis of Fluorine-Containing Boronic Acid Ester Compound

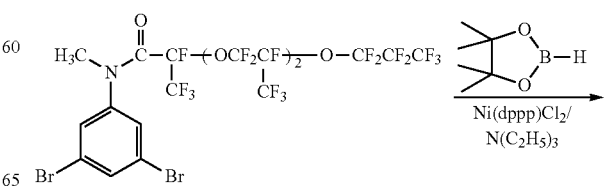

mmol) of triethylamine were dissolved, 8.0 g (62 mmol) of 4,4,5,5-tetramethyl-1,3,2-dioxaborolane was added dropwise at a temperature of 80° C. Subsequently, the temperature was raised to 100° C., and the mixture was reacted in a nitrogen atmosphere for 48 hours. The reaction mixture was cooled to room temperature, and then added to an aqueous saturated ammonium chloride solution to terminate the reaction. Then, a general reaction treatment was carried out, and 19.6 g of a crude product was obtained.

Under reduced pressure (26 Pa), low-boiling-point components were removed at 150° C., 16.9 g (yield based on 3,5-dibromo-N-methylanilide compound: 86%) of a target fluorine-containing boronic acid ester compound [B] was obtained as a transparent and highly viscous liquid slightly tinged with yellow by column chromatography (Wakogel C-300) using a mixed solvent of n-hexane/diethyl ether (volume ratio: 1/1) as an elute.

IR (neat): 2,982 cm$^{-1}$, 1,696 cm$^{-1}$, 1,603 cm$^{-1}$, 1,451 cm$^{-1}$, 1,243 cm$^{-1}$, 1,143 cm$^{-1}$ The following shows the chemical shifts of $^{19}$F-NMR (chemical shift: CFCl$_3$ basis) and $^1$H-NMR (chemical shift: TMS basis), measured in CDCl$_3$:

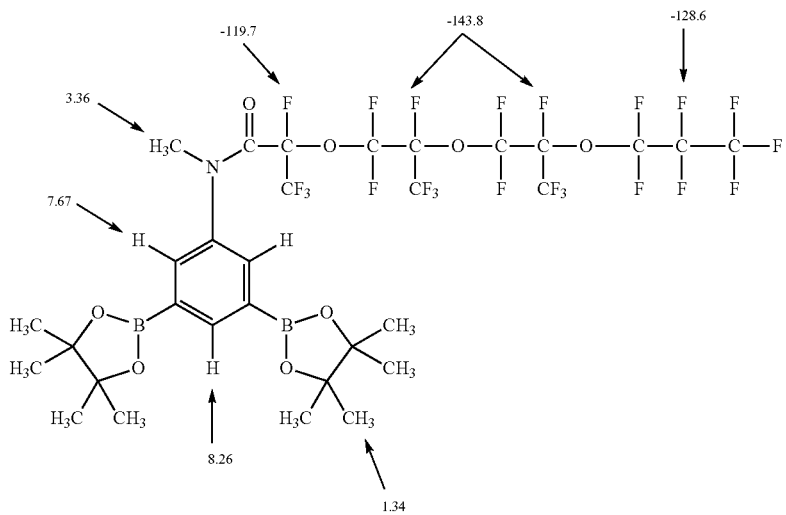

Additionally, when 5 g of the fluorine-containing boronic acid ester compound [B] was added to 10 ml of 1,3-bis(trifluoromethyl)benzene, a homogeneous solution was formed. From this fact, a high solubility in a fluorine-containing organic solvent was confirmed.

Reference Example 3

Example of Use of Fluorine-Containing Polyether Compound as Curing Agent

A fluorine-containing polyether compound of the following formula (100 parts by weight; l+m=100, viscosity (25° C.): 14 Pa·s):

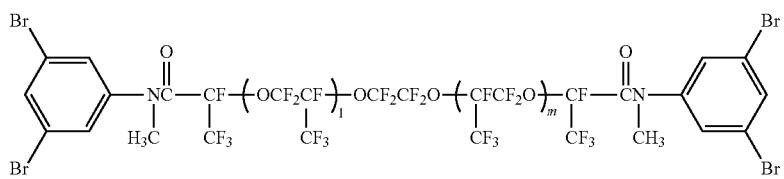

11 parts by weight of the fluorine-containing boronic acid ester compound synthesized in Example 2, 0.033 parts by weight of palladium acetate, 0.076 parts by weight of triphenylphosphine, and 7.4 parts by weight of potassium phosphate were added to a mixed solvent containing 125 parts by weight of ethanol, 25 parts by weight of water, and 400 parts by weight of 1,3-bis(trifluoromethyl)benzene. The mixture was mixed under a nitrogen atmosphere at room temperature for 5 minutes, and under reduced pressure, a volatile substance was removed at room temperature. To this mixture, 13 parts by weight of acetylene carbon black was added. As for the curable composition obtained in this manner, the curing behavior was measured at 130° C. for 30 minutes using a Monsanto disk rheometer.

| | |
|---|---|
| ML | 0.5 dN·m |
| MH | 6.8 dN·m |
| t10 | 0.5 minutes |
| t50 | 1.0 minutes |
| t90 | 2.4 minutes |

The invention claimed is:

1. A fluorine-containing boronic acid ester compound represented by the general formula:

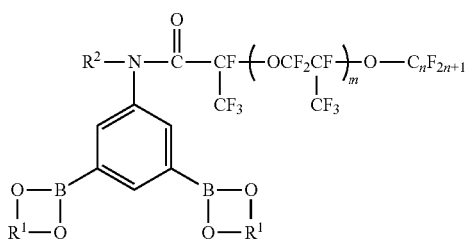

[I]

wherein $R^1$ is a linear or branched divalent aliphatic hydrocarbon group having 2 to 10 carbon atoms, $R^2$ is a hydrogen atom, an alkyl group having 1 to 3 carbon atoms or a phenyl group, n is an integer of 1 to 3, and m is an integer of 0 to 4.

2. The fluorine-containing boronic acid ester compound according to claim 1, wherein in the general formula [I], $R^1$ is a —C(CH$_3$)$_2$C(CH$_3$)$_2$— group.

3. The fluorine-containing boronic acid ester compound according to claim 1, wherein in the general formula [I], $R^2$ is a methyl group.

4. The fluorine-containing boronic acid ester compound according to claim 1, wherein in the general formula [I], n is 3.

5. A method of producing a fluorine-containing boronic acid ester compound represented by the general formula:

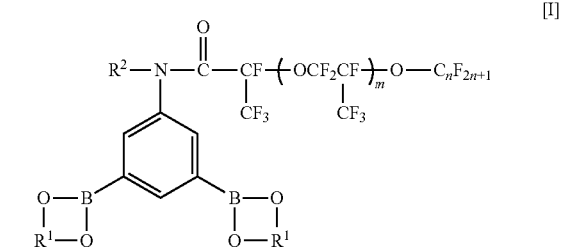

[I]

wherein $R^1$ is a linear or branched divalent aliphatic hydrocarbon group having 2 to 10 carbon atoms, $R^2$ is a hydrogen atom, an alkyl group having 1 to 3 carbon atoms or a phenyl group, n is an integer of 1 to 3, and m is an integer of 0 to 4; the method comprising reacting a fluorine-containing 3,5-dihalogenoanilide derivative represented by the general formula:

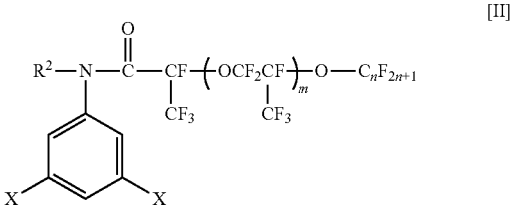

[II]

wherein $R^2$ is a hydrogen atom, an alkyl group having 1 to 3 carbon atoms or a phenyl group, n is an integer of 1 to 3, and m is an integer of 0 to 4, and X is a halogen atom, with a dialkoxyborane represented by the general formula:

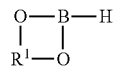

wherein $R^1$ is a linear or branched divalent aliphatic hydrocarbon group having 2 to 10 carbon atoms.

6. The method according to claim 5, wherein in the general formula [II], each X is a bromine atom.

7. The method according to claim 5, wherein the reaction is carried out in the presence of a tertiary amine using a nickel catalyst.

8. The method according to claim 6, wherein the reaction is carried out in the presence of a tertiary amine using a nickel catalyst.

* * * * *